United States Patent [19]

Brain

[11] Patent Number: 5,584,290
[45] Date of Patent: Dec. 17, 1996

[54] COMBINED LARYNGEAL MASK AIRWAY AND MUSCULAR OR NEURO-MUSCULAR RESPONSE DEVICE

[76] Inventor: Archibald I. J. Brain, Sandford House, Fan Ct Gardens, Long-Crops Road, Chertsey, Surrey, United Kingdom, KT16 0DJ

[21] Appl. No.: 550,360

[22] Filed: Oct. 30, 1995

[30] Foreign Application Priority Data

Nov. 3, 1994 [GB] United Kingdom ............... 9422224

[51] Int. Cl.⁶ .............................................. A61M 16/00
[52] U.S. Cl. ............................ 128/207.15; 128/204.22; 128/633; 128/634; 128/639
[58] Field of Search ......................... 128/633, 639, 128/634, 207.14, 207.15, 206.26, 207.16, 200.26, 204.22; 604/96, 103, 174

[56] References Cited

U.S. PATENT DOCUMENTS

| 3,732,868 | 5/1973 | Williams et al. | 128/639 |
|---|---|---|---|
| 4,683,890 | 8/1987 | Hewson | 128/639 |
| 4,907,602 | 3/1990 | Sanders | 128/787 |
| 4,960,133 | 10/1990 | Hewson | 128/784 |
| 5,016,647 | 5/1991 | Sanders | 128/787 |
| 5,125,406 | 6/1992 | Goldstone et al. | 128/642 |
| 5,179,952 | 1/1993 | Buinvicius et al. | 128/642 |
| 5,197,491 | 3/1993 | Anderson et al. | 128/786 |
| 5,241,956 | 9/1993 | Brain | 128/207.15 |
| 5,282,464 | 2/1994 | Brain | 128/207.15 |

Primary Examiner—V. Miller
Assistant Examiner—Eric P. Raciti
Attorney, Agent, or Firm—Hopgood, Calimafde, Kalil & Judlowe

[57] ABSTRACT

An airway device in the form of a modified laryngeal mask is fitted with single, multiple or paired electrodes (herein termed "internal electrodes") so placed as to enable stimulation of or to record a spontaneous degree of activity of selected excitable tissues (a) lying in direct contact with or in close proximity with the mask, or (b) in conjunction with suitably placed body-surface electrodes (herein termed "external electrodes") at one or more body-surface regions known to have muscular, neuro-muscular or other conductive relationship with organs more remotely situated from the mask, such internal electrodes being adapted for flexible connection to external monitoring or stimulating apparatus for diagnostic, therapeutic, palliative or sedative purposes.

20 Claims, 2 Drawing Sheets

COMBINED LARYNGEAL MASK AIRWAY AND MUSCULAR OR NEURO-MUSCULAR RESPONSE DEVICE

BACKGROUND OF THE INVENTION

Laryngeal Mask Airway (LMA) devices are illustratively described in U.S. Pat. Nos. 4,509,514, 4,995,388, 5,249,571, 5,282,464 and others. As airway devices per se, they have been successful in use, differing from the classical endotracheal tube (ETT) in that an LMA features an inflatable ring or cuff which forms a seal with a patient's airway by surrounding the opening into the glottis, instead of passing through the glottis and vocal cords into the windpipe (trachea).

One consequence of these arrangements is that the vocal cords remain free to close when using an LMA, whereas they cannot do so if the patient has been intubated with an ETT. In practice, this means that if anaesthesia is or becomes insufficient and the patient begins to wake up during surgery, pain can stimulate the vocal cords to close, leading in turn to an inability to ventilate the lungs. This usually triggers an alarm on the ventilator (the machine for driving respiratory gases into the patient's lungs), thus alerting the anaesthetist that something is wrong. Such a sequence can occur when using an LMA but it cannot occur when using an ETT; as a result, in use of an ETT, insufficient anaesthesia may progress to the point that the patient becomes aware during anaesthesia but is unable to communicate his awareness to the anaesthetist.

Use of an LMA thus has an advantage over use of an ETT in acting indirectly as a monitor of anaesthetic depth. However, closure of the vocal cords is undesirable because it may result in insufficient oxygen delivery, and it would be preferable to detect the onset of patient pain and/or awareness at an earlier stage, so that corrective action can be taken before oxygen delivery is jeopardized. To some extent, in the inventor's experience, earlier detection is possible, using one or more of the following methods:

1. Setting the pressure alarm on the ventilator at a level only slightly above that recorded when the patient is fully anaesthetized;
2. Measuring the inflation pressure in the LMA cuff, because LMA-cuff pressure is related to the tonic contractile state of muscles surrounding the cuff;
3. Noting any change in the shape of the patient's expired carbon-dioxide tracing, since it is normal practice to continuously measure expired carbon dioxide during anaesthesia; and
4. When suitable equipment is available, measuring the inspiratory and expiratory flow-volume loops, and noting any alteration in loop patterns.

All of these methods are subject to false positive interpretation, and a more specific test of laryngeal muscle activity would be useful.

BRIEF STATEMENT OF THE INVENTION

It is an object of the invention to provide a method and means whereby to more specifically test or monitor laryngeal muscle activity while a patient is under anaesthesia or is otherwise exposed to a potential for involuntary closure of his vocal cords.

Another object is to provide a method and means for electrically detecting an incorrect positioning of an installed LMA by observation of the presence or absence of an expected characteristic muscle-activity signal.

A further object is to meet the above objects in conjunction with concurrent electric-signal detection, measurement or stimulation of one or more body organs remote from an installed LMA, as, for example, the heart or the oesophagus (gullet).

A specific object is to provide means associated with an LMA whereby to permit the administration of electrical stimulation to the region of the larynx and of the lower pharynx at frequencies known to prevent repolarization (recharging) of excitable tissues, thus providing local anaesthesia to the region.

A still further object is to provide means associated with an LMA whereby to influence cerebral cortical activity in conjunction with known scalp-electrode techniques.

The invention achieves the foregoing objects by providing the mask region of an LMA with electrode elements having the adaptive capability of electrical coupling to specific muscles or muscle groups or to specific nerves or nerve groups, whereby to stimulate or to detect and record activity levels of specific organs. Electrical stimulation and/or recording is via flexible-lead connection of the electrode elements to stimulating and/or recording means outside of the patient.

BRIEF DESCRIPTION OF THE DRAWINGS

The invention will be described in detail for a presently preferred embodiment, in conjunction with the accompanying drawings, in which.

DETAILED DESCRIPTION

Figure 1:
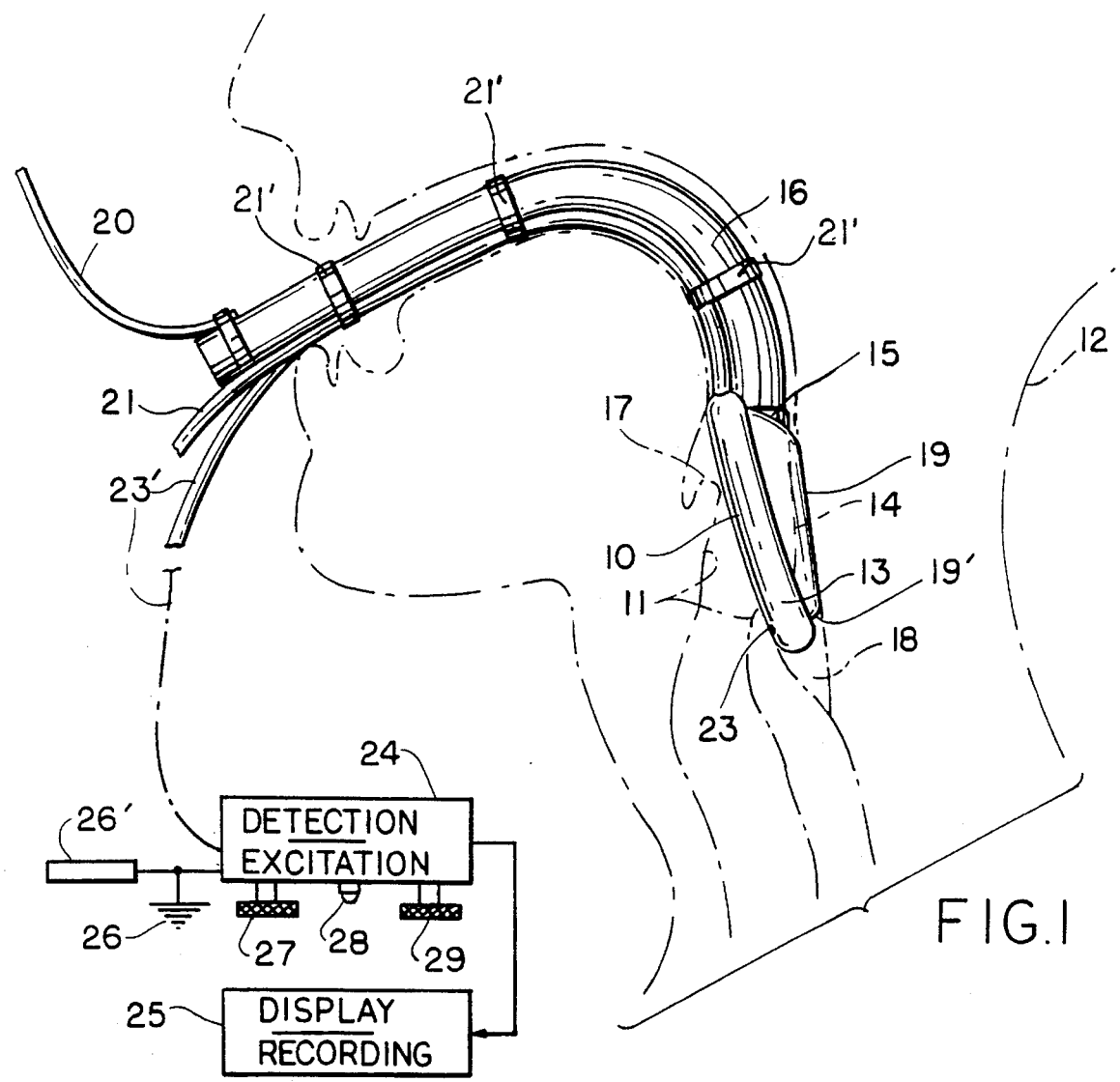
FIG. 1 is a simplified view in schematic side elevation to show a laryngeal mask (LMA) of the invention in installed position in a patient.
Figure 2:
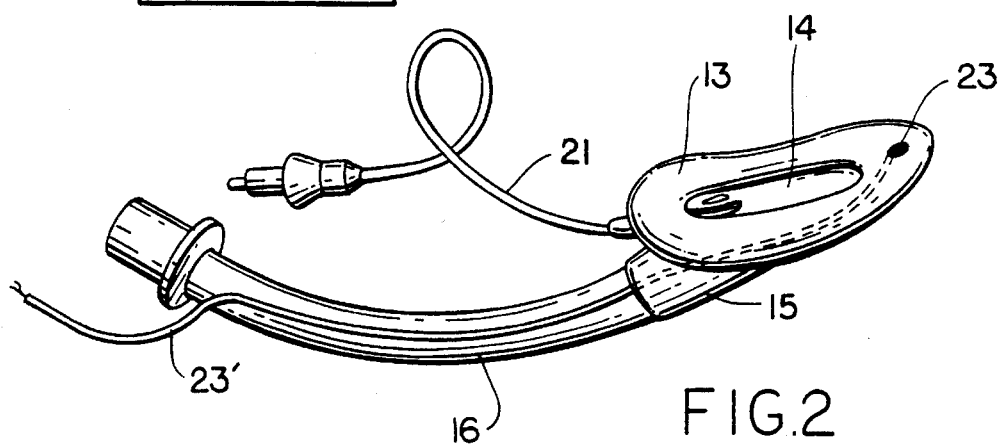
FIG. 2 is a simplified perspective view of a laryngeal mask airway (LMA) device which is generally similar to the LMA device of FIG. 1, the view being taken to show detail of the front side of the device, namely, the side which faces the patient's laryngeal inlet.

In the system of FIGS. 1 and 2, a laryngeal mask 10 is seen to provide peripherally sealed engagement around the laryngeal inlet 11 of a patient 12. Thus sealed, the mask 10 presents a front (or anterior) side facing into the laryngeal inlet, and a back (or posterior) side facing the back wall of the pharynx. The sealed engagement is via an air-inflated annular ring 13 which is connected to a central plate 14 having an inlet airway port formation 15 on a sloping alignment with respect to the general plane of ring 13. An airway tube 16 is connected at its distal end to the port formation 15 and is curved for general conformance with the patient's natural breathing passage via the throat to the pharynx. As shown, the seal to the laryngeal inlet surrounds the epiglottis 17 and has sealed footing at the base 18 of the hypopharynx; also, the sloping back surface of the back plate 14 and port formation 15 are held off the back wall of the pharynx by means of an air-inflated flexible sheet 19 which is peripherally sealed to the back side of the inflatable ring and which upon inflation engages the back wall 19' of the pharynx, to thereby provide a residual forward thrust for enhanced sealing engagement of inflated ring 13 to the laryngeal inlet.

The airway tube 16 may be rigid or stiffly flexible, and a manipulating handle 20 is shown in FIG. 1 at the outer end of tube 16, for facilitating mask insertion into the patient; with the ring 13 in deflated condition, the inflation/deflation procedure is externally controllable via an inflation-air supply tube 21, which in FIG. 1 is shown to be retained by straps 21' to the airway tube 16. The particular mask 10 of FIG. 1 will be understood to be an illustrative one of several varieties, greater detail of which will be found in various of the above-identified patents. For reference purposes, the front or anterior side of mask 10 will be understood to be the side which faces the laryngeal inlet and passage, and the back or posterior side of mask 10 will be understood to be the side which faces the posterior or back wall 19' of the pharynx.

In accordance with the invention, means are provided on and in combination with an LMA whereby to directly and electrically stimulate or detect muscle activity within the body of a patient, via one or more electrodes which, upon proper installation of the LMA, are brought into electrically coupled relation with specific muscles or muscle groups, or specific nerves or nerve groups, or specific organs. As shown in FIGS. 1 and 2, there is but a single such electrode 23, exposed for contact with body tissue when the LMA is correctly installed. Illustratively, the electrode 23 is preferably of platinum, bonded to a desired distal locale on the front side of the inflatable ring, and having a fine-gauge insulated flexible lead-wire connection 23' within the mask and its airway tube 16, to external excitation/detection means 24 and display/recorder means 25; means 24 is schematically shown to be grounded at 26, which in the case of a single electrode will be understood to mean conductive connection at ground potential to an external part of the body, for example, a conductive plate 26'. More specifically, and again illustratively, the electrode 23 is on the longitudinal plane of symmetry of the inflatable ring 13 and on the front side and distal end of the mask; when the mask is properly positioned, electrode 23 will therefore directly and locally contact or confront body tissue (i.e. mucosal surface) overlying the posterior crico-arytenoid muscle.

When wire 23' is connected to remote means 24/25 that is suitable for recording electromyograms (electrical signals emitted from living muscle tissue) and suitable indifferent electrode contact is made (e.g. at 26) with the patient's skin, the correctly placed LMA allows activity of the posterior crico-arytenoid muscle to be visually observed in real time during anaesthesia. The posterior crico-arytenoid muscle is the principal dilator of the vocal cords in man; and during normal inspiration in an awake individual, there is phasic activity of this muscle, which becomes progressively less marked as anaesthesia deepens. For this reason, an observation of the degree of muscle activity in the posterior crico-thyroid during anaesthesia may be used as an indication of the depth of anaesthesia. In addition, the degree of activity of this muscle may be used as an indication of the extent of neuro-muscular blocking-drug activity, when such paralysing agents are being used to facilitate muscular relaxation during surgery.

Stimulation of the posterior crico-arytenoid muscle may also be carried out according to this form of the invention, with the object of testing its function in conjunction with ventilatory flow loops or alternatively with the object of opening the glottis when it is in a state of spasm, a state known as laryngospasm which is a feared complication of general anaesthesia. As a stimulator, the means 24, 25, 26 will be understood to provide a suitable electric signal or signals to electrode 23, upon appropriate mode selection at 27 and signal on/off control at 28.

Figure 3:
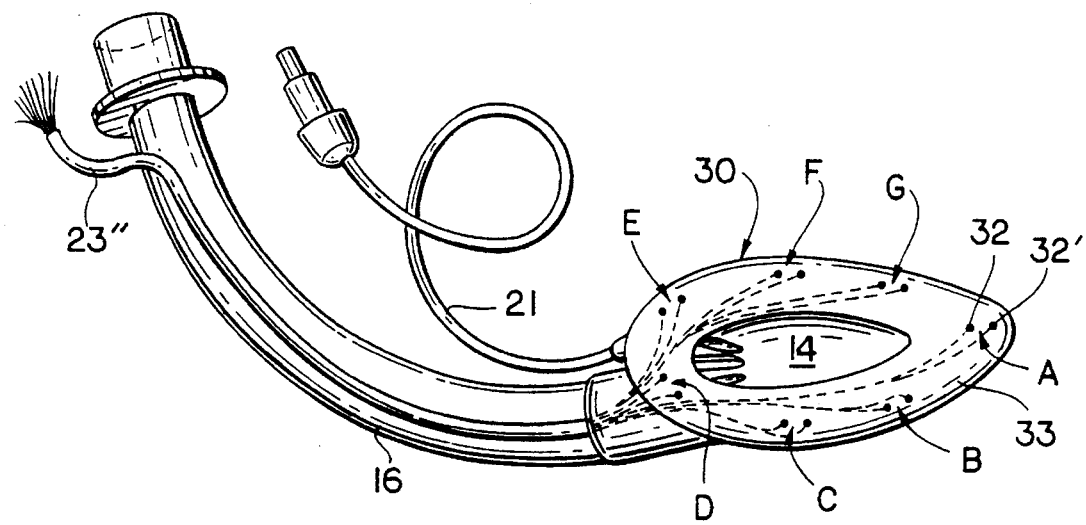
FIG. 3 is a view similar to FIG. 1, to show a modification.

It should be noted that the electrode position described in the above example is only one of a variety of possible arrangements, for example single, multiple or paired electrodes may be placed to stimulate or record activity in any of the twenty-five muscle groups or the three major nerves lying within the area surrounding the LMA mask, for diagnostic or therapeutic purposes, or indeed, and preferably, when used in conjunction with suitably placed body-surface electrodes, to detect or stimulate the activity of more remote organs such as the oesophagus or heart. By way of example, FIG. 3 shows an LMA 30 having an inflatable ring 31 with multiple paired electrodes 32, 32' at each of a series of spaced locations A, B . . . G along the locus of sealed inflatable-ring (33) engagement of the installed mask to the laryngeal inlet. Each of the electrodes of each pair has its own insulated flexible-wire connection to the external means 24, 25; all such connecting wires are contained within a single cable 23" which can be deemed to be symbolized at 23' in FIG. 1, it being understood that manual selection at 29 will enable selection of the electrode pair, or individual electrode, or differently located electrodes to be available for particular muscle activity to be observed or stimulated.

Illustratively, the particularly selected paired electrodes of FIG. 3 can serve for making differential diagnosis of laryngeal dysfunction, or for administering stimulating current in the micro-ampere range at frequencies known to reversibly suspend neuro-muscular activity by preventing repolarization of excitable tissues, for example, at frequencies at or near 4000 Hz. An object of such high-frequency stimulation can be to relax the larynx in the event of laryngospasm, or to palliate pain or discomfort, as when the discomfort is attributable to maintaining the LMA in place in an awake patient.

In an unpublished recent work by the present inventor, it has been found experimentally that stimulation of an anaesthetized baboon pharynx via an electrode 40 (FIG. 4) placed in a caudad position at the distal end of an LMA 41, and using excitation signals at frequencies close to the alpha and beta range of cerebral cortical activity, results in a phenomenon of cerebral-wave orchestration, such that cerebral activity appears to become synchronized or regularized to conform with the applied frequency. This effect is of unknown clinical significance and is likely to require the presence of scalp electrodes. But the fact that similar frequencies in the form of light bursts to the human retina may cause tranquilizing effects in the awake human subject indicates a possible further utility for the presently modified LMA, in respect of inducing a useful degree of sedation which might supplement general anaesthesia or facilitate toleration of the device in an awake subject.

Figure 4:
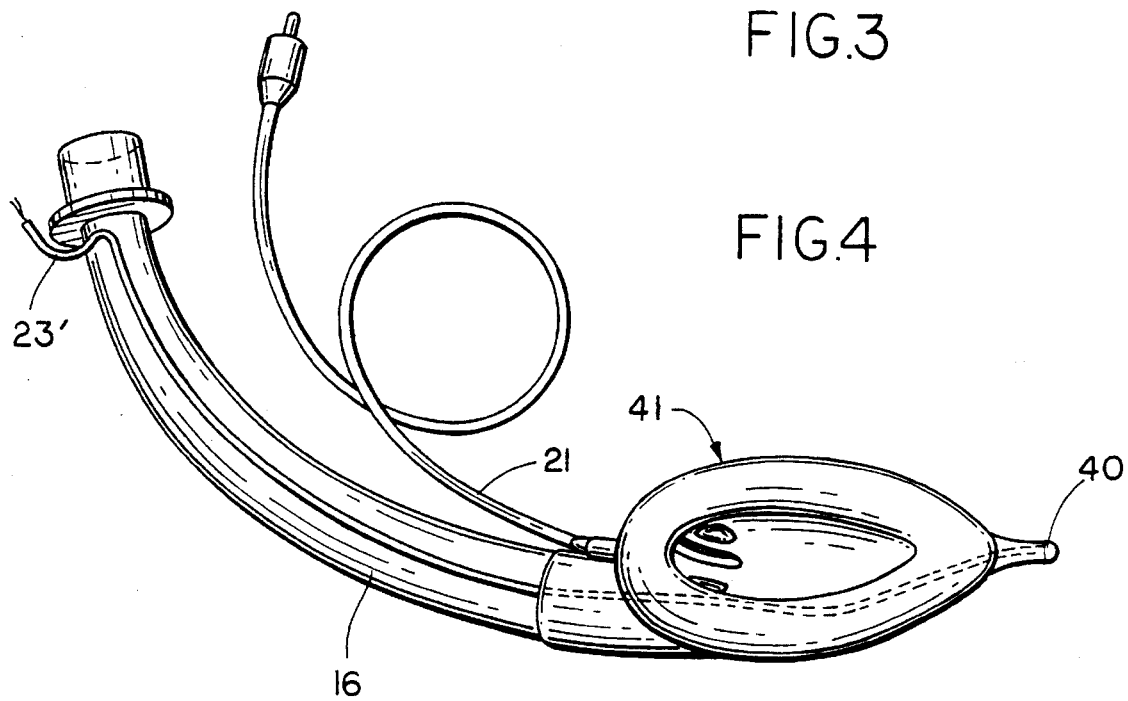
FIG. 4 is another view similar to FIG. 1, for another modification.

Animal experiments have also demonstrated the feasibility of altering the muscular tone in the oesophagus (gullet) using a prototype according to the present invention during anaesthesia, in which an electrode 40 is placed in the position shown in FIG. 4. This finding may have utility in reducing the danger of regurgitation of stomach contents during anaesthesia.

What is claimed is:

1. In combination, a laryngeal mask having a front side and a back side and means including an outer portion of said front side for establishing peripherally sealed engagement of said mask around the laryngeal inlet of a patient, with the front side facing into the laryngeal inlet and the back side facing the back wall of the pharynx, an elongate airway tube having a distal end which establishes a sealed passage through said mask between the back and front sides of said mask, electrode means locally carried by said mask within the outer portion having said sealed engagement, and means including at least one flexible lead to said electrode means for external coupling of a portion of the laryngeal inlet to external electric circuitry.

2. The combination of claim 1, in which the peripherally sealed outer portion of said front side includes a distal-end portion for sealed contact with a local portion of the hypopharyngeal surface, and in which said electrode means comprises at least one electrode within said distal-end portion.

3. The combination of claim 1, in which said electrode means comprises plural spaced electrodes within said peripherally sealed outer portion of the front side of said mask.

4. The combination of claim 1, in which said laryngeal mask has a distal-end formation projecting distally beyond the outer portion having said peripherally sealed engagement, and in which said electrode means includes at least one electrode carried by said distal-end formation and adapted for body-tissue engagement within the upper oesophageal sphincter.

5. The combination of claim 1, in which said electrode means comprises a series of separate electrodes in distributed array within said peripherally sealed outer portion of the front side of said mask.

6. The combination of claim 5, in which said electrodes are in paired grouping.

7. The combination of claim 1, in which said electrode means for said at least one flexible lead comprises the distal end of said flexible lead.

8. The combination of claim 7, in which the material of said electrode means is platinum.

9. In combination, a laryngeal mask having a front side and a back side and means including an outer portion of said front side for establishing peripherally sealed engagement of said mask around the laryngeal inlet of a patient, with the front side facing into the laryngeal inlet and the back side facing the back wall of the pharynx, an elongate airway tube having a distal end which establishes a sealed passage through said mask between the back and front sides of said mask, said mask and the sealed airway passage therethrough having a longitudinally extending central plane of symmetry which extends between proximal and distal ends of said mask for symmetry of the peripherally sealed engagement on opposite sides of said central plane, and electrode means locally carried by said mask at intercept with said central plane and within the distal end of the outer portion having said sealed engagement, and means including at least one flexible lead to said electrode means for external coupling of a portion of the hypopharyngeal surface to external electric circuitry.

10. The combination of claim 19, in which said electrode means is a pair of closely spaced electrodes each of which has an independent flexible lead for coupling to the external circuitry.

11. The combination of claim 9, in which said electrode means is a single electrode.

12. An artificial airway device to facilitate a patient's lung ventilation, comprising an airway tube and a laryngeal mask at one end of said tube, said mask having a front side and a back side and a first inflatable cuff formation in a generally elliptical configuration extending from a proximal end to a distal end and adapted upon inflation to achieve a peripheral seal of the front side of said mask to and around the laryngeal inlet of a patient, electrode means including at least one tissue-engageable electrode locally within a portion of the peripheral seal, and a second inflatable cuff formation on the back side of said mask, said second cuff formation in inflated condition being adapted to engage the back wall of the pharynx and thereby to compressionally load said electrode into local tissue engagement while also enhancing the peripheral seal of the front side of said mask.

13. The artificial airway device of claim 12, in which said first inflatable cuff formation includes a distal-end region adapted for contact with the hypopharyngeal surface, and in which said electrode means further includes at least one electrode carried by said distal-end region, said second inflatable cuff formation being sufficiently extensive in the distal direction to enable at least a degree of compressional preload of said distal-end electrode in application to tissue of the hypopharyngeal surface.

14. The method of therapeutically treating or monitoring an existing muscular or neuromuscular condition of a patient, which method comprises:

(a) selecting and installing a laryngeal mask having an airway tube with a distal end having an inflatable cuff formation for inflated peripherally sealed engagement to the patient's laryngeal inlet, said cuff formation having electrode means in local contact with body tissue by reason of cuff inflation to seal the laryngeal mask for exclusive airway-tube communication with the patient's airway; and (b) using said electrode means in conjunction with external electrical circuitry to monitor and/or to affect a muscular or neuromuscular condition of the patient.

15. The method of claim 14, wherein step (b) consists in using said electrode means in conjunction with a conductive grounding connection to an exterior surface portion of the body.

16. The method of monitoring the depth of an anaesthetized condition of a patient in the course of an operative procedure, which method comprises:

(a) selecting and installing a laryngeal mask having an airway tube with a distal end having an inflatable cuff formation for inflated peripherally sealed engagement to the patient3s laryngeal inlet, said cuff formation having electrode means in local contact with body tissue by reason of cuff inflation to seal the laryngeal mask for exclusive airway-tube communication with the patient3s airway, said electrode means being so positioned on said mask as to have local contact with the patient3s crico-arytenoid muscle when said mask is correctly positioned in the patient;

(b) anaesthetizing the patient; and (c) using said electrode means in conjunction with external electrical circuitry to monitor activity of the crico-arytenoid muscle in real time during the anaesthesia.

17. The method of claim 16, for the case of a surgical operation in which a neuro-muscular blocking agent has been administered to facilitate muscular relaxation during surgery, and wherein step (c) additionally comprises use of the external electrical circuitry to stimulate the posterior crico-arytenoid muscle to open the glottis in avoidance or reduction of a state of laryngospasm.

18. In combination, a laryngegal mask having a front side and a back side and means including an outer portion of said front side for establishing peripherally sealed engagement of said mask around the laryngeal inlet of a patient, with the front side facing into the laryngeal inlet and the back side facing the back wall of the pharynx, an elongate airway tube having a distal end which establishes a sealed passage through said mask between the back and front sides of said mask, said laryngeal mask having a distal-end formation projecting distally beyond the outer portion having said peripherally sealed engagement, electrode means including at least one electrode carried by said distal-end formation and adapted for body-tissue engagement within the upper oesophageal sphincter, and means including at least one flexible lead to said electrode means for external coupling of a portion of the laryngeal inlet to external electric circuitry.

19. The method of monitoring the depth of an anaesthetized condition of a patient in the course of an operative procedure, which method comprises:

(a) selecting and installing a laryngeal mask having an airway tube with a distal end having an inflatable cuff formation for inflated peripherally sealed engagement to the patient's laryngeal inlet, said cuff formation having electrode means in local contact with body tissue by reason of cuff inflation to seal the laryngeal mask for exclusive airway-tube communication with the patient's airway;

(b) using said electrode means in conjunction with external electrical circuitry to determine a first level of selected parameter response upon initial completion of an anaesthetized condition of the patient; and (c) thereafter using said circuitry to monitor said parameter response for a predetermined change from said first level.

20. The method of therapeutically treating or monitoring an existing muscular or neuromuscular condition of a patient, which method comprises:

(a) selecting and installing a laryngeal mask having an airway tube with a distal end having an inflatable cuff formation for inflated peripherally sealed engagement to the patient's laryngeal inlet, said cuff formation having electrode means with at least two separate electrodes in spaced relation and in local contact with body tissue by reason of cuff inflation to seal the laryngeal mask for exclusive airway-tube communication with the patient's airway; and (b) using both of said electrodes concurrently in conjunction with external electrical circuitry to monitor and/or to affect a muscular or neuromuscular condition of this patient.

* * * * *